United States Patent [19]

Maeda et al.

[11] Patent Number: 5,110,729

[45] Date of Patent: * May 5, 1992

[54] METHOD OF PRODUCING PEPTIDES USING BACULOVIRUS VECTORS IN CULTURED CELLS

[75] Inventors: Susumu Maeda, Tottori; Mitsuru Furusawa, Tokyo; Yasumasa Marumoto, Tokyo; Tadashi Horiuchi, Tokyo; Yoshinari Sato, Tokyo; Yoshiyuki Saeki, Tokyo, all of Japan

[73] Assignee: Daiichi Seiyaku Co., Ltd., Tokyo, Japan

[*] Notice: The portion of the term of this patent subsequent to Jan. 22, 2002 has been disclaimed.

[21] Appl. No.: 641,795

[22] Filed: Jan. 16, 1991

Related U.S. Application Data

[63] Continuation of Ser. No. 930,489, Nov. 14, 1986, abandoned.

[30] Foreign Application Priority Data

Nov. 14, 1985 [JP] Japan .................................. 60-255607

[51] Int. Cl.$^5$ ...................... C12P 21/00; C12N 15/00; C12N 15/20; C12N 15/34
[52] U.S. Cl. ................................. 435/69.1; 435/320.1; 435/172.3; 435/69.51; 435/235.1
[58] Field of Search ................. 435/69.1, 320.1, 172.3, 435/235.1, 69.51; 536/27; 935/60, 32, 36, 64, 70

[56] References Cited

U.S. PATENT DOCUMENTS 4,745,051 5/1988 Smith et al. ...................... 435/69.51

OTHER PUBLICATIONS

Morishita et al., J. Biochem., 109, 36–44, (1991).
Miller, (1982), in *Genet. Eng. in Euk.*, pp. 89–97.
Rohrmann et al., (1981), J. Mol. Evol., 17, 329–333.
Pennock et al., (1984), Mol. Cell. Biol.. 4:399–406.
S. Maeda, "Characteristics of Human Interferon–Alpha Produced by a Baculovirus Vector in the Silkworm, *Bombyx mori*", Proc. Japan Acad., vol. 60, No. 10, 423–426, (1984).
G. Smith, "Production of Human Beta Interferon in Insect Cells Infected with a Baciluvirus Expression Vector", Molecular and Cellular Biology, vol. 13, No. 12, 2516–2165, (1983).
R. Matthews, "Classification and Nomenclature of Viruses. Third Report of the International Committee on Taxonomy and Viruses", S. Karger, Basel, 170–171, (1979).

*Primary Examiner*—Richard A. Schwartz
*Assistant Examiner*—S. L. Nolan
*Attorney, Agent, or Firm*—Sughrue, Mion, Zinn, Macpeak & Seas

[57] ABSTRACT

Recombinant *Bombyx mori* nuclear polyhedrosis viruses having, in the polyhedral protein-encoding structural gene portion of the *Bombyx mori* nuclear polyhedrosis virus DNA (BmNPV DNA), a structural gene for a desired protein as joined to the whole of or a part of the polyhedral protein-encoding structural gene with or without interposition of a linker base sequence are provided.

By propagating the above viruses in silkworm-derived cells or silkworms, fused proteins of a desired protein and the whole of or a part of the polyhedral protein as joined together with or without interposition of a linking amino acid or peptide are produced. The desired proteins can be obtained from the fused proteins by cleavage or decomposition at the linking site.

28 Claims, 7 Drawing Sheets

METHOD OF PRODUCING PEPTIDES USING BACULOVIRUS VECTORS IN CULTURED CELLS

This is a continuation of application Ser. No. 06/930,489 filed Nov. 14, 1986, now abandoned.

FIELD OF THE INVENTION

This invention relates to recombinant *Bombyx mori* (silkworm) nuclear polyhedrosis viruses and a method of producing peptides using such recombinant viruses.

BACKGROUND OF THE INVENTION

A method of producing peptides by utilizing *Bombyx mori* nuclear polyhedrosis virus (BmNPV) has already been reported (Reference 1; for the references cited herein, see the end hereof).

The central feature of this method consists in constructing a recombinant BmNPV with a structural gene for a desired protein replacing the polyhedral protein-encoding structural gene portion using recombinant DNA techniques and propagating the recombinant in cultured silkworm (*Bombyx mori*) cells or in living silkworms (*Bombyx mori*) to thereby accumulate the desired protein therein. However, this method is still unsatisfactory with respect to the yields of the desired proteins.

Moreover, the production of fused proteins is already in practice in *Escherichia coli*. The yields cannot be said to have been improved significantly, however (References 2-8).

SUMMARY OF THE INVENTION

The present invention is thus concerned with a recombinant *Bombyx mori* nuclear polyhedrosis virus having, in the polyhedral protein-encoding structural gene portion of the *Bombyx mori* nuclear polyhedrosis virus DNA, a structural gene for a desired protein joined to the whole of or a part of the polyhedral protein-encoding structural gene with or without interposition of a linker base sequence.

The present invention is also concerned with a method of producing a fused protein by propagating the recombinant virus in cultured *Bombyx mori* cells or in living *Bombyx mori*.

The invention is further concerned with a method of producing the desired protein by cleaving or decomposing the fused protein at the linking site thereof.

BRIEF DESCRIPTION OF THE DRAWING

In the accompanying drawings.

DETAILED DESCRIPTION OF THE INVENTION

BmNPV is widely known among sericulturists. The strain T3 is a typical strain isolated by the present inventors. The viral DNA (BmNPV DNA) of this strain has been deposited with the ATCC in the USA receiving accession number ATCC 40188.

For isolating a portion containing the structural gene for polyhedral protein from this viral DNA, treatment with EcoRI treatment is suitable, among others, as described in Reference 1. An *Escherichia coli* strain (*E. coli* K12JM83 DGB-0036) carrying the plasmid pBmE36 with an EcoRI-EcoRI fragment (about 10.5 kb) of the viral DNA being inserted in the plasmid at the EcoRI cleavage site has been deposited with the Fermentation Research Institute, Agency of Industrial Science and Technology, Ministry of International Trade and Industry of Japan, receiving accession number FERM BP-813.

Furthermore, as described in Reference 1, pBmE36, when treated with HindIII, gives an approximately 3.9 kb-long fragment containing the structural gene for polyhedral protein. The fragment is then inserted into the commercially available plasmid pUC9 (commercially available from Pharmacia P-L Biochemicals). The subsequent EcoRI cleavage, Bal31 treatment (whereby fragments differing in length can be produced by adjusting the treatment time) and further HindIII cleavage, or a like procedure provides a fragment comprising the whole of or a part of the polyhedral protein gene.

A structural gene for a desired protein can be joined to the whole of or a part of the polyhedral protein gene by using an appropriate linker (DNA) (Reference 19) and the fused protein produced, when cleaved by an appropriate means at the site of the peptide or amino acid (linking portion) translated in correspondence to the linker base sequence, gives the desired protein, which can then be isolated by conventional methods. When the fused protein is useful per se, naturally a cleavage procedure is not required. In such case, the linker may be absent.

Well known, among others, as the peptide or amino acid (linking portion) corresponding to the linker and the means of cleaving or decomposing the same are the sequence Ile-Glu-Gly-Arg and the blood coagulation factor Xa (hereinafter abbreviated as "F-Xa") capable of cleaving the sequence; Pro-Ama-Gly-Pro (wherein Ama is any kind of amino acid) and collagenase capable of cleaving the sequence; Arg or Phe and trypsin capable of cleaving the peptide bond behind the same; Tyr or Phe and chymotrypsin capable of cleaving the peptide bond behind the same; Pro-Arg and thrombin capable of cleaving the peptide bond behind the same; tryptophan and N-bromosuccinimide capable of decomposing the same; and methionine and cyanogen bromide capable of decomposing the same (References 2-10). The linking portion and the means of cleavage or decomposition are not limited to those mentioned above and many other appropriate combinations of various peptides or amino acids and various chemical or enzymatic methods may also be employed for the linking portion and the cleavage or decomposition means, respectively.

Desirably, the desired protein should not contain any peptide or amino acid which can be decomposed upon exposure to a linking portion cleavage or decomposition process such as mentioned above. However, it is also possible to decompose the fused protein restrictively using appropriately restricted, moderate conditions to thereby achieve the object.

The term "desired protein" as used herein can be a eukaryotic protein, preferably a mammalian protein. Specific examples of the desired protein include various physiologically active substances and substances useful as diagnostic reagents, such as interferons (IFNs), tumor necrosis factor (TNF), interleukins and other lymphokines, insulin, growth hormone and other hormones, hepatitis vaccine, influenza vaccine and various other antigen proteins, tissue plasminogen activating factor (TPA), somatomedins, enzymes useful for industrial use such as steroid converting enzymes, acylases, amylases, lipases, and the like, food additives and feed additives, among others. Some of these materials may have a sugar chain added thereto. In accordance with the invention, peptides are produced in eukaryotic cells. When a gene derived from a eukaryote is used, the peptide produced can undergo the same modification or modifications as that or those occurring in vivo in the eukaryote. Therefore, the products produced in this invention can be said to have higher utility as compared with those produced in bacteria.

The genes coding for these proteins may be chromosomal DNAs isolated from naturally occurring materials, cDNAs prepared through the intermediary of nature-derived mRNAs, chemically synthesized DNAs, or DNAs produced by an appropriate combination of the techniques for the examples just mentioned (References 18 and 19).

In case a product somewhat differs in amino acid sequence (substitution, deletion or addition) from the contemplated material but still has the required functions such as physiological activity, modification may intentionally be made to such effect. For instance, when methionine is to be decomposed with cyanogen bromide in relation to the linking portion mentioned above, the methionine residue or residues occurring in the desired protein can be replaced with another amino acid residue or other amino acid residues or can be deleted. In this case, it is advisable that the peptide produced on the basis of the base sequence designed in line with the above concept is examined as to whether the activity thereof is suitable for the intended purpose or not.

In certain instances, part of an amino acid residue may remain in the desired protein product as seen, for instance, in the case of the chemical decomposition of cysteine with 2-nitro-5-thiocyanobenzoic acid. In this case, too, the product should advisably be examined for activity as mentioned above to thereby determine whether the product is suitable for the intended purpose or not.

Plasmids (plasmids for recombination) with a base sequence comprising the whole of or a part of the polyhedral protein gene of the Bombyx mori nuclear polyhedrosis virus DNA (BmNPV DNA) and a structural gene for a desired protein as joined together (either with or without interposition of a linker), namely a gene for a fused protein, being inserted therein can be produced employing conventional recombinant DNA techniques using those plasmids, restriction enzymes and other materials that are commercially available. Production of such plasmids can be routinely achieved by reference to the examples to be described later herein.

For producing recombinant viruses using the above plasmids, cells of an established Bombyx mori cell line are subjected to mixed infection with a plasmid for recombination and BmNPV, if necessary followed by recombinant virus isolation by the plaque method (Reference 11) or the dilution method (Reference 12), for instance. Suitable established Bombyx mori cell lines which can be used include known Bm cells (BM-N cells described in References 1, 11 and 13; deposited under ATCC No. CRL-8910) and BM-N cells deposited under ATCC No. CRL-8851, among others. For producing a desired material in silkworms, silkworms are subjected to viral infection by injecting the virus (either a mixture of the recombinant and nonrecombinant viruses or the recombinant virus isolated therefrom) propagated in cultured cells thereinto percutaneously or into the body cavity thereof, or by giving the virus with feed through mouth. Then the silkworms are fed on an artificial feed or mulberry leaves for an appropriate number of days to thereby accumulate the desired fused protein. Generally, the fused protein is not soluble in water and suspended in the silkworm body fluid and can be separated or purified by conventional manners such as chromatography (ion-exchange resin, affinity, gel-permeation, etc.), centrifugation, extraction and the like.

When the silkworm is ground down and mixed with a solvent such as SDS aqueous solution, urea aqueous solution, aqueous alkaline solution and the like or is ground down in the presence of such solvent, the fused protein can be separated or purified by a manner as described above from the solution. When the fused protein is to be cleaved, the cleavage/decomposition procedure may be performed in the manner as described above.

The following examples in which insulin-like growth factors (IGF-I and IGF-II) and α-interferon are the desired proteins are given to illustrate the present invention in further detail. It is to be noted, however, that these examples are by no means intended to restrict the scope of the invention. The schemes for plasmid construction are outlined in FIGS. 1–5. Unless otherwise specified, the 5' (upstream) side of the DNA sequence is shown on the left side and the 3' (downstream) side on the right in accordance with conventional practice.

Synthesis, cleavage, screening, isolation and other treatments of the polyhedral protein gene, genes for desired proteins and genes for fused proteins can be performed by using the techniques described in Reference 1 as well as gene manipulation techniques in conventional use (cf. e.g. References 18 and 19).

EXAMPLE 1

A. Construction of Plasmid Deprived of Polyhedrin Gene

The plasmid pBmE36 (Reference 1) was cleaved with EcoRI and the cleavage product was rendered blunt-ended using DNA polymerase I (Klenow fragment) in the presence of dNTPs (four deoxynucleoside triphosphate species). Partial digestion with HindIII followed by agarose gel electrophoresis gave a polyhedrin gene-containing fragment. Using T4 ligase, this fragment was ligated with a pUC9 fragment, which had been prepared by cleaving pUC9 (available from Pharmacia P-L Biochemicals) with EcoRI, rendering the cleavage product blunt-ended using Klenow fragment and further cleaving with HindIII, to produce a ligation product. The ligation product obtained was used for transforming Escherichia coli K-12JM83. The plasmid was then recovered and designated p9BmE36. (The above method is described in Reference 19.)

An EcoRV recognition site and an AatI recognition site were introduced into p9BmE36 at the site of the initiation codon ATG and the site of the termination codon TAA, respectively, by in vitro mutagenesis (Reference 14). Thus, p9BmE36 was treated with DNase I in the presence of ethidium bromide to produce a nicked plasmid (Reference 14), which was then annealed with the following two chemically synthesized DNA fragments:

Subsequent treatment with polymerase I and T4 ligase gave a heteroduplex plasmid, which was then used for transforming *Escherichia coli* K-12JM83. The transformation was performed again for obtaining a desired mutant. Thus a plasmid, p9BmM36 was obtained.

For polyhedrin gene elimination from p9BmM36 and polylinker insertion, the following two DNA fragments (each 38mer) were chemically synthesized:
CTAAGAGCTCCCGGGAATTCCATGGATATC-TAGATAGG and
CCTATCTAGATATCCATGGAATTCCCG-GGAGCTCTTAG These two fragments are complementary to each other and have SacI, SmaI, EcoRI, NcoI, EcoRV and XbaI recognition sites.

The above two fragments were phosphorylated at the respective 5' end using T4 kinase and then annealed together. The annealed product was ligated, in the presence of T4 ligase, with a polyhedrin gene-free fragment obtained by cleavage of p9BmM36 with EcoRV and AatI. This procedure resulted in formation of a BglII recognition site and an AatI recognition site on the 5' side and on the 3' side of the linker, respectively. The resultant plasmid was used for transforming *Escherichia coli* K-12JM83 and then recovered and designated pBM030.

The DNA sequence of and the cleavage sites on the polylinker portion of pBM030 are shown below as contrasted with the polyhedrin gene portion of p9BmE36.

B. Construction of Plasmid Having Partly Deficient Polyhedrin Gene

The plasmid p9H13 (Reference 1) was cleaved with EcoRI and then treated with Ba131 to thereby pare off a part of either side of the cleavage site. By varying the time of Ba131 treatment, fragments differing in length were produced. These fragments were treated with HindIII and separated by 0.7% agarose gel electrophoresis, followed by extraction, which gave various virus-derived DNA fragments differing in length.

Plasmid pUC9 was treated with SmaI and HindIII, followed by ligation with the DNA fragments previously obtained (having a blunt end and a HindIII end). Using the plasmids thus produced, *Escherichia coli* K-12JM83 was transformed, and then grown. The plasmide were recovered, and the base sequence from the 3' side of each virus-derived insert DNA fragment was determined by the dideoxy method (Reference 15) using a primer (15-base sequencing primer for M13) to thereby identify the viral polyhedral gene portion. Thus, a base sequence corresponding to the amino acid sequence of polyhedral protein as described by Serebryani et al. (Reference 16) was found among the base sequences of the virus-derived DNA fragments. The translational start codon ATG and the termination codon TAA were also identified.

Among the various plasmids (p9B series plasmids) obtained depending on the length of time of Ba131 treatment, the ones with 212 bp, 338 bp, 662 bp and 727bp downstream from the translational start codon ATG for the polyhedrin gene being missing were designated p9B240, p9B120, p9B115 and p9B086, respectively. The polyhedrin gene has a length of 738 bp inclusive of the stop codon TAA.

| 123 | | | 40 |
|---|---|---|---|
| <u>ATG</u>CCGAATT | ATTCATACAC | CCCCACCATC | GGGCGTACTT |
| ACGTGTACGA | CAATAAATAT | TACAAAAACT | TGGGCTGTCT |
| TATCAAAAAC | GCCAAGCGCA | AGAAGCACCT | AGTCGAACAT |

| | | | |
|---|---|---|---|
| GAACAAGAGG | AGAAGCAATG | GGATCTTCTA | GACAACTACA |
| TGGTTGCGCA | AGATCCCTTT | TTAGGACCGG | GCAAAAACCA |
| AAAACTTACC | C\|TTTTTAAAG | AAATTCGCAG | TGTGAAACCC |
| | p9B240 ⇐⎦ | | |
| GATACCATGA | AGTTAATCGT | CAACTGGAGC | GGCAAGAGT |
| TTTTGCGTGA | AACTTGGACC | CGTTTTGTTG | AGGACAGCTT |
| CCCCATTGTA | AACGACC\|AAG | AGGTGATGGA | CGTGTACCTC |
| | p9B120 ⇐⎦ | | |
| GTCGCCAACC | TCAAACCCAC | ACGCCCCAAC | AGGTGCTACA |
| AGTTCCTCGC | TCAACACGCT | CTTAGGTGGG | AAGAAGACTA |
| CGTGCCCCAC | GAAGTAATCA | GAATTATGGA | GCCATCCTAC |
| GTGGGCATGA | ACAACGAATA | CAGAATTAGT | CTGGCTAAAA |
| AGGGCGGCGG | CTGCCCAATC | ATGAACATCC | ACAGCGAGTA |
| CACCAACTCG | TTCGAGTCGT | TTGTGAACCG | CGTCATATGG |
| GAGAACTTCT | ACAAACCCAT | CGTTTACATC | GGCACAGACT |
| CTGCCGAAGA | AGAGGAAATC | C\|TAATTGAGG | TTTCTCTCGT |
| | p9B115⇐⎦ | | |
| TTTCAAAATA | AAGGAGTTTG | CACCAGACGC | GCCTCTGTTC |
| ACTGGT\|CCGG | CGTAT<u>TAA</u> | | |
| p9B086 ⇐⎦ | | | |

C. Construction of Gene for Fused Protein Composed of α-Interferon and Polyhedral Protein pIFN2B310 (Reference 1) was cleaved with SmaI and an α-IFN-J fragment was isolated by agarose gel electrophoresis. This was ligated with SmaI-cleaved pBM030 using T4 ligase and the resultant plasmid was used for transmitting *Escherichia coli* K-12JM83. The recombinant plasmid was designated pBT310 after confirming that it had the α-IFN-J gene inserted in the correct direction.

pBT310 was cleaved with BglII and the cleavage product was rendered blunt-ended using a Klenow fragment in the presence of dNTPs and then cleaved with ScaI. An α-IFN-J gene-containing fragment was isolated by agarose gel electrophoresis.

p9B086 was cleaved with EcoRI and ScaI and a polyhedrin gene-containing fragment was isolated by agarose gel electrophoresis. This fragment was rendered blunt-ended using S1 nuclease and ligated with the above-mentioned α-IFN-J gene-containing fragment using T4 ligase. *Escherichia coli* K-12JM83 was transformed with the resultant plasmid. It was then confirmed by the dideoxy method that the DNA sequence of the linking portion in the plasmid thus obtained was correct. The plasmid was designated pIFNF086.

The DNA sequence of the linking portion was: ,180

D. Construction of Gene for Fused Protein Composed of IGF-I and Polyhedral Protein The plasmid pIGF001 was recovered from *Escherichia coli* K12 MC1061 IGF001 (FERM BP-932) and cleaved with SAII. The cleavage product was rendered blunt-ended using the Klenow fragment in the presence of dNTPs and cleaved with AvaII, and an IGF-I gene-containing fragment was isolated by polyacrylamide gel electrophoresis.

Separately, pBM030 was cleaved with EcoRV and SacI.

It appeared the amino acid sequence Ile-Glu-Gly-Arg should be introduced between polyhedral protein and IGF-I in the production of a fused protein so that the fused protein could be recognized and cleaved by the blood coagulation factor Xa (F-Xa). For that purpose, the following two DNA fragments were chemically synthesized:

ATTGAAGGCAGAG (13mer) and
GACCTCTGCCTTCAATAGCT (20mer).

These two fragments are complementary to each other and, after annealing, form, on the upstream side, a cohesive end linkable with a SacI cleavage end and, on the downstream side, a cohesive end linkable with an AvaII cleavage end.

These two fragments were phosphorylated each at the 5' end using T4 kinase and then annealed together. The annealed product, the above-mentioned IGF-I fragment and the above-mentioned cleaved pBM030 were ligated together using T4 ligase. *Escherichia coli* K-12JM83 was transformed with the ligation product to produce a plasmid. DNA sequencing by the dideoxy method confirmed that the linkage between the F-Xa recognition site and the IGF-I gene in this plasmid (pIFG-I030) was correct. pIGF-I030 was cleaved with BolII, then rendered blunt-ended using the Klenow fragment in the presence of dNTPs, and cleaved with ScaI, and an IGF-I gene-containing fragment was isolated by agarose gel electrophoresis.

Separately, p9B086 was cleaved with EcoRI and ScaI and rendered blunt-ended using S1 nuclease, and a polyhedrin gene-containing fragment was isolated by agarose gel electrophoresis and ligated with the IGF-I gene-containing fragment mentioned above using T4 ligase. Using the resultant plasmid, *Escherichia coli* K-12JM83 was transformed, and a plasmid having the fused protein gene constructed by correct ligation was obtained and designated pIGF-IF086. The DNA sequence of the linking portion is shown below.

```
--------Polyhedrin gene       ------GGTGGGGATCTAAGAGCT--
ATT----GAA----GGC----AGA----GGT----CCA----GAA----ACC----TTG----
Ile----Glu----Gly----Arg----Gly----Pro----Glu----Thr----Leu----
       |_______ F-Xa _______|    |_____________ IGF-I _____________
```

E. Construction of Genes for Fused Proteins Composed of IGF-II and Polyhedral Proteins Differing in Length The plasmid pIGF002 was recovered from *Escherichia coli* K12 MC1061 IGF002 (FERM BP-933), partially digested with SalI, rendered blunt-ended using the Klenow fragment in the presence of dNTPs and then cleaved with HaeIII, followed by polyacrylamide gel electrophoresis, whereby an IGF-II gene-containing fragment was isolated. This fragment was ligated with SmaI-cleaved pBM030 using T4 ligase and the ligation product was used for transformation of *Escherichia coli* K-12JM83. For the transformant thus obtained, the transformant was confirmed to carry a plasmid (pIGF-II030) with the IGF-II gene inserted therein in the correct direction.

pIGF-II030 was partially digested with EcoRI and then cleaved with ScaI, and an IGF-II gene-containing fragment was isolated by agarose gel electrophoresis This fragment was ligated, in the presence of T4 ligase, with a fragment containing a part of the polyhedrin gene as isolated by agarose gel electrophoresis after cleavage of each of p9B 240, p9B120 and p9B115 with EcoRI and ScaI.

*Escherichia coli* K-12JM83 was transformed with the resultant plasmids. DNA sequencing by the dideoxy method confirmed that the plasmids borne by the resultant transformants had the respective fused protein genes constructed in the right way.

These plasmids were designated pIGF-IIF240, pIGF-IIF120 and pIGF-IIF115, respectively.

The DNA sequence of the linking portion in each plasmid is shown below:

pIGF-IIF240

```
  --ACCC|GGGAATTC--ATG--GCT--------
240 <---|
              Met--Ala------IGF-II
``` pIGF-IIF120

```
  --GACC|GGGAATTC--ATG--GCT--------
120 <---|
              Met--Ala------IGF-II
``` pIGF-IIF115

```
  --ATCC|GGGAATTC--ATG--GCT--------
115 <---|
              Met--Ala------IGF-II
```

EXAMPLE 2

Transfection of Bm Cells

The BmNPV T3 strain viral DNA (ATCC No. 40188) and pIFNF086, in a mole ratio of 1:100, were mixed with the solutions I and II having the following compositions, respectively:

| I. Distilled water | 2.1 ml |
|---|---|
| Carrier DNA (salmon testis, 1 mg/ml) | 50 μl |
| BmNPV DNA | 10 μl |
| pIFNF086 DNA | 50 μg |
| 2 M Calcium chloride | 300 μg |
| II. 50 mM HEPES buffer (pH 7.1) containing 0.28 M sodium chloride | 2.5 ml |
| Phosphate buffer (35 mM Na$_2$HPO$_4$-35 mM NaH$_2$PO$_4$) | 50 μl |

A 1-ml portion of the resultant suspension was added to 4 ml of a Bm cell culture medium (TC-10 medium containing 10% fetal calf serum; Reference 17) and the mixture was added to Bm cells (ATCC No. CRL-8910, 2×10$^6$ cells) to thereby introduce the above DNA into Bm cells. Twenty hours later, the medium was replaced with a fresh portion. After further incubation for 5 days, the medium was recovered and centrifuged, and the supernatant was subjected to plaque assay (Reference 11), whereby the recombinant virus was recovered as a clone. This was designated vIFNF086.

Recombinant virus clones, vIGF-IF086, vIGF-IIF240, vIGF-IIF120 and vIGF-IIF115, were obtained in the same manner as above using pIGF-IF086, pIGF-IIF240, pIGF-IIF120 and pIGF-IIF115, respectively.

EXAMPLE 3

Expression of Fused Protein in 3m Cells

Bm cells (ATCC No. CRL-3910, 2×10$^6$ cells; were infected with vIFNF086 by adding thereto a vIFNF086 suspension (5×10$^7$ pfu). Thirty minutes later, the supernatant was discarded, a fresh 4.5 ml portion of medium was added and incubation was continued at 25° C. for 4 days. Thereafter, the culture was centrifuged (1,000 rpm, 10 minutes) to obtain a precipitate. A fresh 500-μl portion of the medium was added to the precipitate and, after five repetitions of a freezing-thawing cycle, the mixture was centrifuged (15,000 rpm, 10 minutes). To the precipitate thus collected, 200 μl of 4% sodium dodecyl sulfate (SDS)-10% mercaptoethanol was added. A 5-μl portion of the resultant solution was used as a sample for SDS-14% acrylamide gel electrophoresis.

After electrophoresis, a band corresponding to the expected fused protein was observed on the gel. Therefore, the density of the band was measured using a densitometer and compared with the density of each marker (each marker band containing 1 µg of protein) The yield thus estimated was 0.3 mg per milliliter of the cell culture broth first obtained. Since the IFN portion accounts for about 40% in this fused protein on a molecular weight basis, this yield reasonably should correspond to an IFN yield of 0.12 mg/ml after successful cleavage and IFN recovery. This yield is more than 20 times higher when compared with the value of $5 \times 10^6$ units/ml (which corresponds to 0.005 mg/ml) as given in a report on the expression of IFN in *Bombyx mori* cells (Reference 1).

The yields of fused proteins produced by Bm cells infected with vIGF-IF086, vIGF-IIF240, vIGF-IIF120 and vIGF-IIF115 as measured in the same manner as described above were 0.5 mg, 0.1 mg, 0.4 mg and 0.5 mg per milliliter of cell culture broth, respectively or, when expressed in terms of the quantity of IGF-I or IGF-II contained in these fused proteins, 0.1 mg/ml, 0.05 mg/ml, 0.1 mg/ml and 0.1 mg/ml, respectively.

EXAMPLE 4

A. Expression of Fused Protein Bm cells

Bm cells (ATCC No. CRL-8910, $2 \times 10^6$ cells) were infected with vIGF-IIF120 by adding thereto a vIGF-IIF120 suspension ($5 \times 10^7$ pfu). Thirty minutes later, the virus was removed, a fresh 4.5-ml portion of medium was added, incubation was continued at 25° C. for 4 days and the culture broth was centrifuged (1,000 rpm, 10 minutes). To the precipitate thus collected, 500 µl of fresh medium was added. After five repetitions of a freezing-thawing cycle, the mixture was centrifuged (15,000 rpm, 10 minutes) to obtain a precipitate. This precipitate was washed with distilled water, dissolved in 0.5% SDS, and subjected to high performance liquid chromatography [HPLC: TSK Gel Phenyl 5PWRP manufactured by Toyo Soda Manufacturing Co., Ltd ); solvent system: 0.1% trifluoroacetic acid-20-75% acetonitrile with a linear concentration gradient]. Thus a 2-ml fraction containing the fused protein was collected.

B. Cleavage with Cyanogen Bromide (BrCN)

To this fraction was added 50 µl of 1% SDS, the mixture was concentrated to dryness, and the concentrate was dissolved in 50 µl of distilled water. To a 15-µl portion of the solution were added 35 µl of formic acid and 45 µl of 70% formic acid, followed by further addition of 5 µl of a cyanogen bromide solution (200 µmol/ml) in 70% formic acid. After 24 hours of reaction at room temperature, the reaction mixture was concentrated to dryness, the concentrate was dissolved in 7.5 µl of distilled water, and the solution was subjected to electrophoresis, whereupon a band corresponding to IGF-II was detected.

Figure 8:
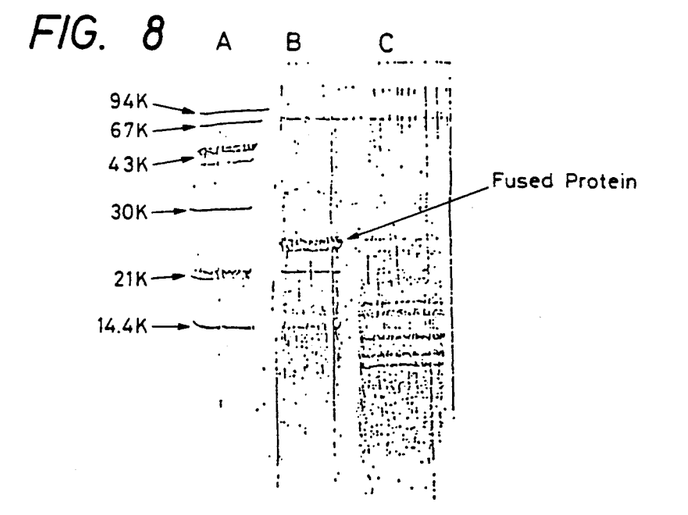

Thus, in SDS-16% polyacrylamide gel electrophoresis, the fraction obtained by extraction of vIGF-IIF120-infected Bm cells with an aqueous SDS solution and the subsequent partial purification by high performance liquid chromatography gave an about 23K band corresponding to the fused protein composed of the polyhedral protein (partial) and IGF-II, while the cyanogen bromide decomposition product showed an about 7K band corresponding to IGF-II together with several bands at 10-14K presumably due to decomposition products from the polyhedral protein (see FIG. 8; wherein A is markers, B is the fused protein and C is the cyanogen bromide decomposition product).

C. Determination of the N-terminal of IGF-IP

In a similar manner as described above, about 20 mg of the fused protein was obtained from a 50 ml culture of Bm cells infected with vIGF-IIF120 and the fused protein was cleaved with cyanogen bromide and the reaction mixture was concentrated.

The concentrate was dissolved in 5 ml of 200 mM pyridine-acetic acid buffer (pH 3.0), and the solution was subjected to column chromatography [SP-Toyopearl (produced by Toyo Soda Manufacturing Co., Ltd.); solvent system: 200 mM pyridine-acetic acid buffer (pH3.0)-2.0M pyridineacetic acid buffer (pH5.0) with a linear concentration gradient]. Thus, a fraction containing IGF-II was collected. This fraction was lyophilized, dissolved in distilled water, and subjected to high performance liquid chromatography [HPLC: ODS-120T (manufactured by Toyo Soda Manufacturing Co., Ltd.); solvent system: 0.1% trifluoroacetic acid-10-65% acetonitrile with a linear concentration gradient]. The pure IGF-II obtained was subjected to peptide sequencing [470A Protein Sequencer (manufactured by Applied Biosystems)]. The amino-terminal amino acid sequence of IGF-II thus confirmed is shown bellow.

Ala Tyr Arg Pro Ser Glu Thr Leu Cys Gly Gly Glu

Leu Val Asp Thr Leu Gln Phe Val Cys Gly Asp Arg

Gly Phe Tyr Phe Ser Arg Pro Ala Ser

EXAMPLE 5

A. Expression of Fused Protein in Bm Cells

The plasmid pIGF001 was recovered from *Escherichia coli* K12 MC1061 IGF001 (FERM BP-932) and cleaved with SalI. The cleavage product was rendered blunt-ended using the Klenow fragment in the presence of dNTPs and cleaved with AvaII, and an IGF-I gene-containing fragment was isolated by polyacrylamide gel electrophoresis.

Separately, pIGF-IIF120 was cleaved with EcoRV and EcoRI to remove the IGF-II gene-containing fragment.

It appeared the amino acid sequence Gly-Pro-Ala should be introduced repeatedly between polyhedral protein and IGF-I in the production of a fused protein so that the fused protein could be recognized and cleaved by a collagenase, which recognizes the amino acid sequence Pro-Ama-Gly-Pro (Ama: any kind of amino acid) and cleaves between Ama and Gly. For that purpose, the following two DNA fragments were chemically synthesized:

AATTGGGCCCAGCTGGTCCAGCTGGTCCCGCGGGTGAATTCATTGAAGGCAGAG
(54mer)

GACCTCTGCCTTCAATGAATTCACCCGCGGGACCAGCTGGACCAGCTGGGCCC (53mer)

These two fragments are complementary to each other and, after annealing, form. on the upstream side. a cohesive end linkable with an EcoRI cleavage end and, on the downstream side a cohesive end linkable with a AvaII cleavage end.

These two fragments were phosphorylated each at the 5' end using T4 kinase and then annealed together. The annealed product, the above-mentioned IGF-I fragment and the above-mentioned cleaved pIGF-IIF120 were ligated together using T4 ligase. *Escherichia coli* K-12JM83 was transformed with the ligation product to produce a plasmid and designated pIGF-IF120. DNA sequencing by the dideoxy method confirmed that the linkage between the collagenase recognition site and the IGF-I gene in this plasmid was correct. The DNA sequence of the linking portion is shown below.

C. Determination of the N-terminal of IGP-IP

The fraction containing IGF-IP was concentrated and the concentrate was subjected to high performance liquid chromatography [HPLC: RPSC (manufactured by Beckman Co.); solvent system: 0.1% trifluoroacetic acid-10-65% acetonitrile with a linear concentration gradient]. The pure IGF-IP obtained was subjected to peptide sequencing [470A Protein Sequencer (manufactured by Applied Biosystems)], and it was revealed that the fused protein had been cleaved by collagenase at the expected site. The amino-terminal amino acid sequence of IGF-IP thus confirmed is shown below.

Gly—Pro—Ala—Gly—Glu—Phe—Ile—Glu—Gly—Arg—Gly—Pro—Glu—Thr—Leu—

Cys—Gly—Ala—Glu—Leu

EXAMPLE 6

Expression of Polyhedrin-IGF-I Fused Protein in Silkworms of (*Bombyx mori*)

In a similar manner as described in EXAMPLE 2, recombinant virus vIGF-IF120 was obtained using pIGFIF120.

In a similar manner as described in EXAMPLE 4 (a), Bm cells were infected with vIGF-IF120 and after freezing-thawing the Bm cells collected from a 50 ml culture broth, the cells were cetrifuged (15,000 rpm, 10 minutes) to obtain a precipitate. This precipitate was dissolved in 6M guanidine hydrochloride solution and centrifuged (15 000 rpm, 5 minutes) to remove a residue. The solution was dialyzed against distilled water and the resulting precipitate was collected by centrifugation (15,000 rpm, 10 minutes).

B. Cleavage with Collagenase

Thus obtained precipitate was dissolved in 800 μl of 10M urea solution followed by addition of 100 μl of 200 mM calcium chloride, 200 μl of 250 mM tris-hydrochloride buffer (pH 7.4) and 900 μl of collagenase solution (produced by Sigma Chemical Co.) (1,500 μ/ml). After incubation for 2 hours at 30° C., this mixture was cetrifuged (15,000 rpm, 5 minutes) to collect a supernatant. This supernatant was subjected to ion-exchange chromatography [DEAE-Toyopearl (manufactured by Toyo Soda Manufacturing Co., Ltd.); solvent system: 25 mM tris-hydrochloride buffer (pH 7.4)]. Thus a fraction containing IGF-I with extra amino acid residues at the amino terminus (hereinafter abbreviated as "IGF-IP") was collected.

Silkworms (*Bombyx mori*) on day 1 of the 5th instar were percutaneously injected with a vIGF-IF086 suspension at a dose of 0.5 ml/head ($10^7$ pfu) and then fed on mulberry leaves at 25° C. for 3 days. Then, a collecting needle was inserted into the abdominal appendage and the body fluid was collected into an ice-cooled Eppendorf tube. The body fluid was centrifuged (15,000 rpm, 10 minutes), the sediment was dissolved in 200 μl of 4% SDS-10% mercaptoethanol, and a 2-μl portion of the resultant solution was used as a sample for SDS-14% acrylamide gel electrophoresis. A band corresponding to the fused protein was noted on the gel after electrophoresis. Therefore, the density of the band was measured using a densitometer and compared with the density of each marker (each band containing 1 μg of protein). The yield thus estimated was 5 mg per milliliter of body fluid. (Molecular weight-based calculation indicates that IGF-I might be recovered in a yield of 1 mg/ml after separation of IGF-I from this fused protein.)

Figure 1:
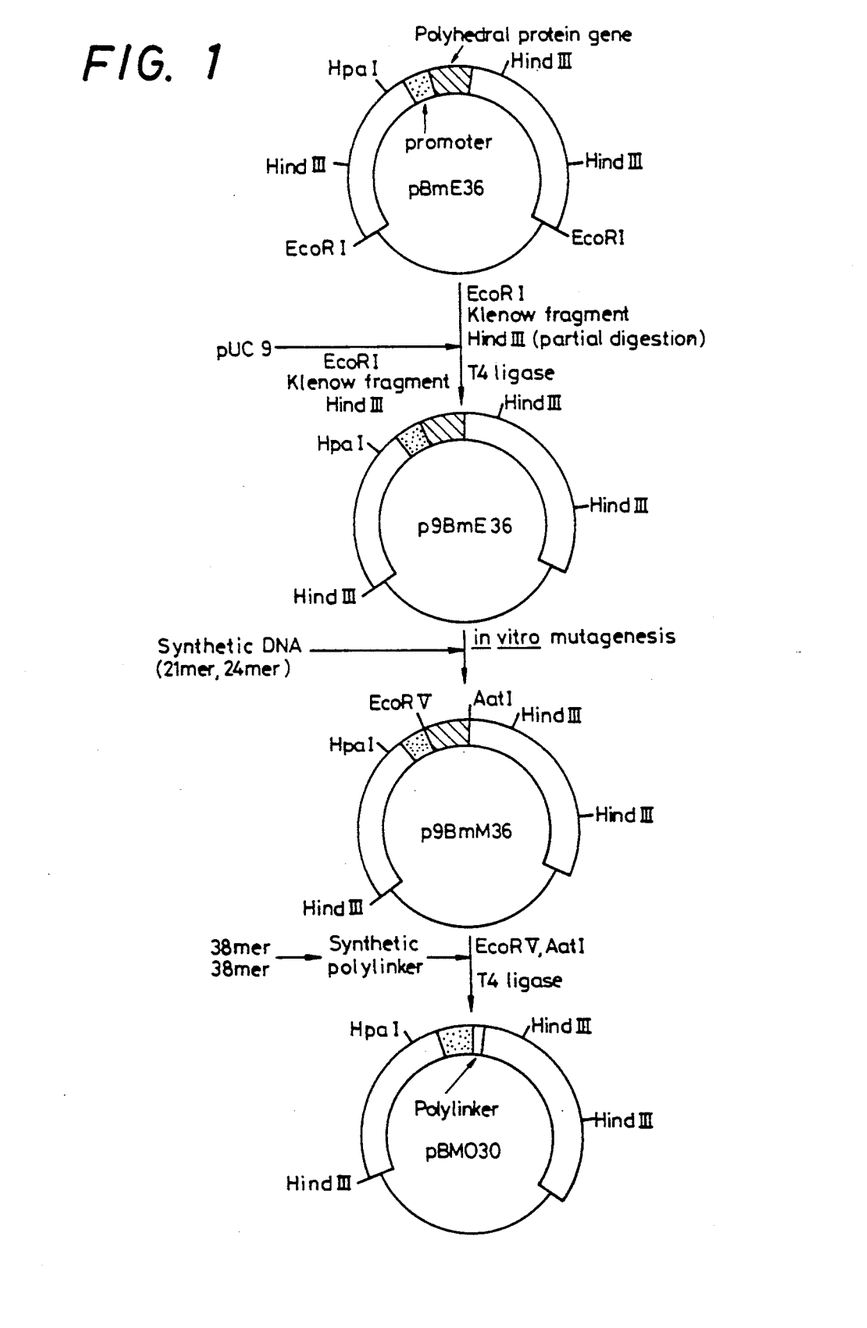
FIG. 1–6 schematically show the construction schemes for certain plasmids for recombinant virus production, given by way of an example.
Figure 2:
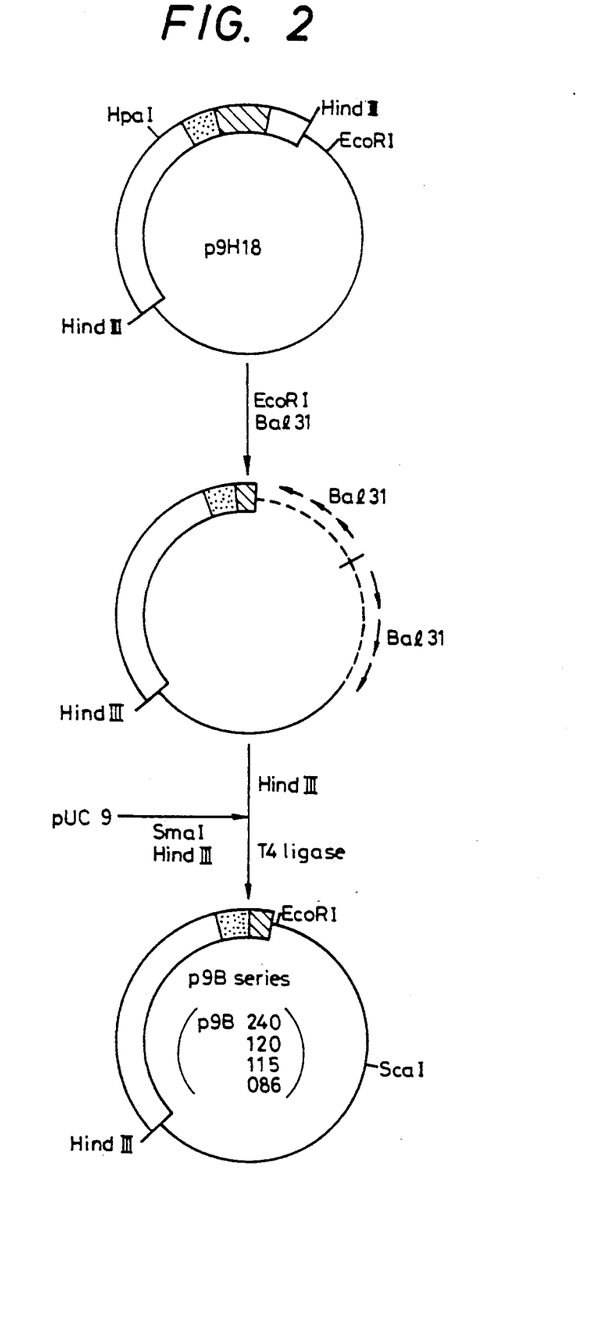
Figure 3:
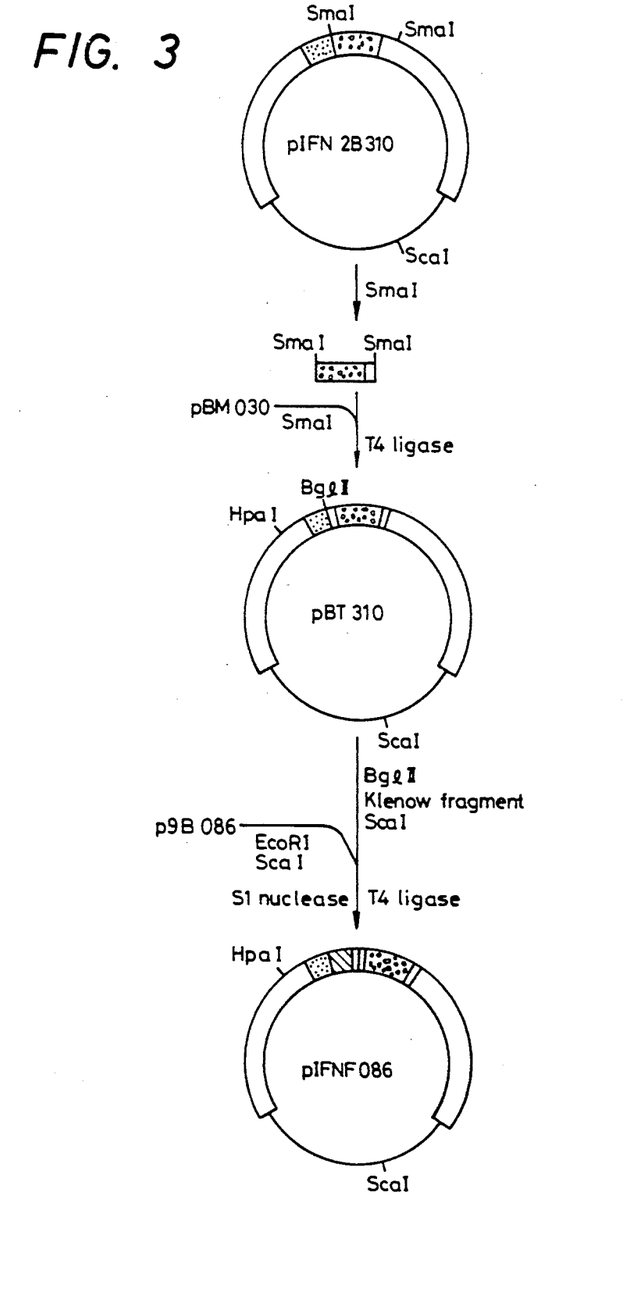
Figure 4:
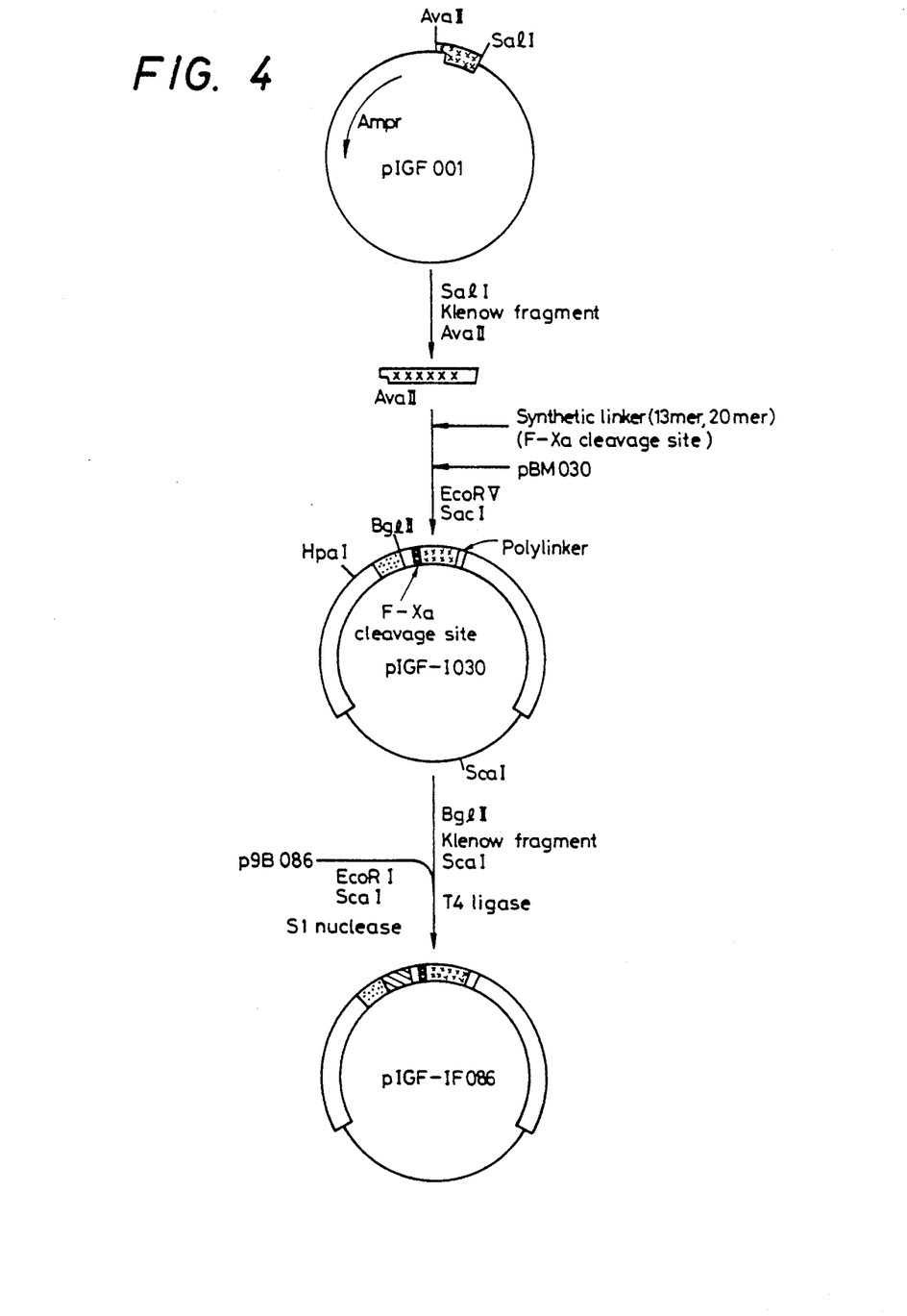
Figure 5:
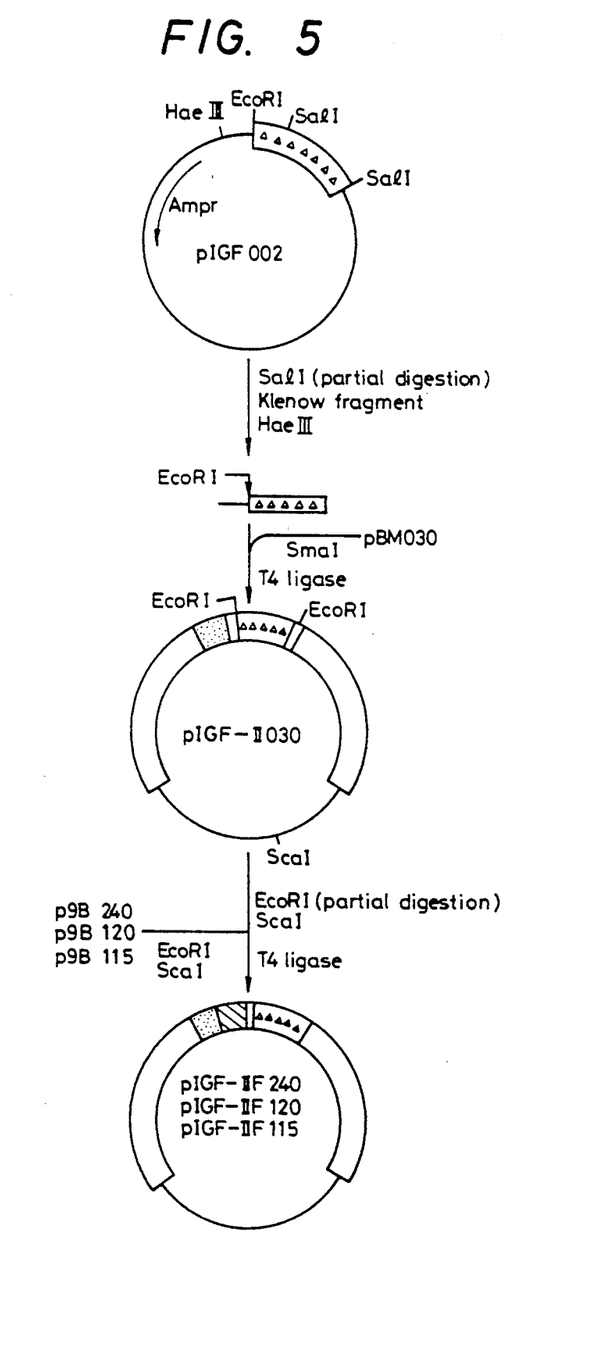
Figure 6:
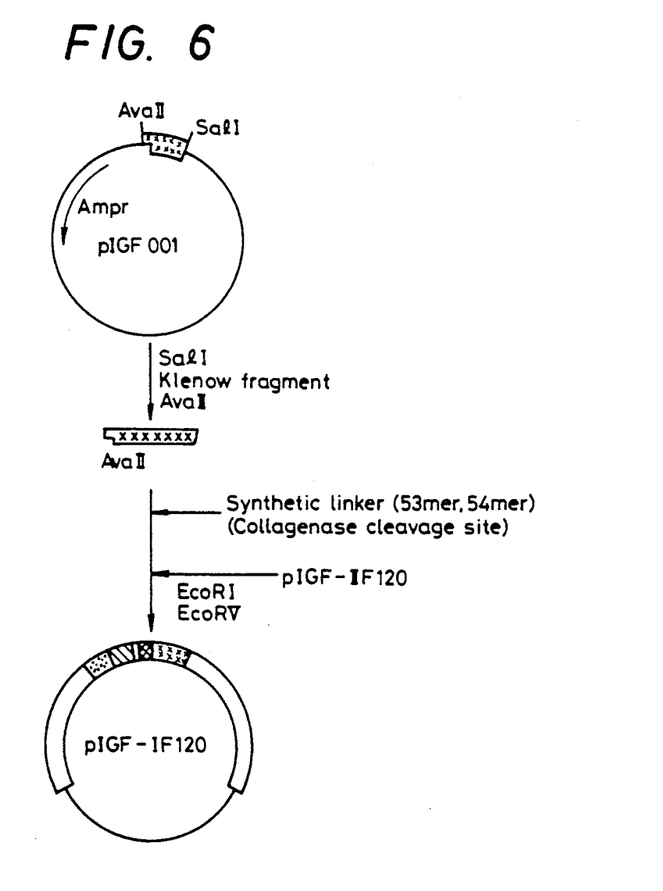
Figure 7:
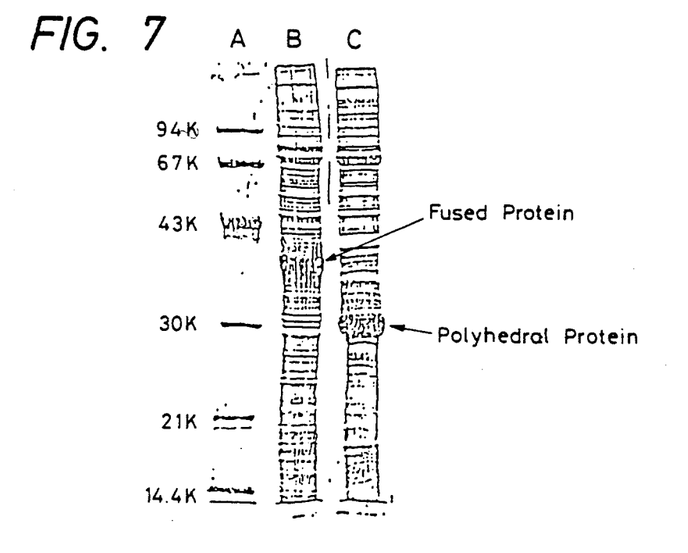
FIG. 7 and 8 show the electrophoretic pattern of the desired fused protein isolated in Examples 6 and 4, respectively.

In SDS-14% polyacrylamide gel electrophoresis, the body fluid obtained from BmNPV-T3 strain-infected silkworms gave a distinct band at about 30K corresponding to polyhedral protein, whereas the body fluid from vIGF-IF086-infected silkworms did not given any band corresponding to polyhedral protein but showed an about 36K band characteristic of the fused protein composed of polyhedral protein and IGF-I (see FIG. 7; wherein A is markers, B is body fluid infected with vIGD-IF086 and C is body fluid infected with BmNPV-T3).

The DNA sequence each of the synthetic gene for IGF-I and the synthetic gene for IGF-I as used in the above examples is shown below together with the corresponding amino acid sequence.

IGF-I

```
            Gly Pro Glu Thr Leu Cys Gly
---TCGAATTC ATG GGT CCA GAA ACC TTG TGT GGT

Ala Glu Leu Val Asp Ala Leu Gln Phe Val Cys
GCT GAA TTG GTT GAC GCT TTG CAA TTC GTT TGT

Gly Asp Arg Gly Phe Tyr Phe Asn Lys Pro Thr
GGT GAC AGA GGT TTC TAC TTC AAC AAG CCA ACT

Gly Tyr Gly Ser Ser Ser Arg Arg Ala Pro Gln
GGT TAC GGA TCC TCT TCC AGA AGA GCT CCA CAA

Thr Gly Ile Val Asp Glu Cys Cys Phe Arg Ser
ACT GGT ATC GTC GAT GAA TGT TGT TTC AGA TCT

Cys Asp Leu Arg Arg Leu Glu Met Tyr Cys Ala
TGT GAC TTG AGA AGA TTG GAA ATG TAC TGT GCT

Pro Leu Lys Pro Ala Lys Ser Ala
CCA TTG AAG CCA GCT AAG TCT GCT TAG TCGACTG
```

IGF-II

```
         Ala Tyr Arg Pro Ser Glu Thr Leu
---AATTC ATG GCT TAC AGA CCA TCT GAA ACC TTG

Cys Gly Gly Glu Leu Val Asp Thr Leu Gln Phe
TGT GGT GGT GAA TTG GTC GAC ACC TTG CAA TTC

Val Cys Gly Asp Arg Gly Phe Tyr Phe Ser Arg
GTT TGT GGT GAC AGA GGT TTC TAC TTT TCC AGA

Pro Ala Ser Arg Val Ser Arg Arg Ser Arg Gly
CCA GCC TCC AGA GTT TCT AGA AGA TCC AGA GGT

Ile Val Glu Glu Cys Cys Phe Arg Ser Cys Asp
ATC GTC GAA GAA TGT TGT TTC AGA TCC TGT GAC

Leu Ala Leu Leu Glu Thr Tyr Cys Ala Thr Pro
TTG GCT TTG TTG GAA ACT TAC TGT GCC ACC CCA

Ala Lys Ser Glu
GCC AAG TCC GAA TAG---
```

References

1: *Nature*, 315, 592 (1985)
2: *Science*, 198, 1056 (1977)
3: Japanese Patent Application (OPI) No. 145289/79 (The term "OPI" as used herein means an "unexamined published application ".)
4: Japanese Patent Application (OPI) No. 19092/80
5: Japanese Patent Application (OPI) No. 45395/80
6: Japanese Patent Application (OPI) No. 104886/80
7: Japanese Patent Application (OPI) No. 145221/81
8: Japanese Patent Application (OPI) No. 166200/81
9: *Nature*, 309, 810 (1984)
10: *Nature*, 285, 456 (1980)
11: *J. Seric. Sci. Jpn*, 53, 547 (1984)
12: *J. Invertebr. Pathol.*, 29., 304 (1977)
13: *Appl. Envion. Microbiol.*, 44, 227 (1982)
14: *Nucleic Acids Res.*, 9, 3647 (1981)
15: *Science*, 214, 1205 (1981)
16: *J. Invertebr. Pathol.*, 30, 442 (1977)
17: *J. Invertebr. Pathol.*, 25, 363 (1975)
18: *Am. J. Hum. Genet.*, 31, 531 (1979)
19: T. Maniatis et al.: *Molecular Cloning:* Cold Spring Harbor Laboratory (1982)

What is claimed is:

1. A method for producing a peptide which comprises:
    (a) constructing a recombinant *Bombyx mori* nuclear polyhedrosis virus comprising the following elements, operatively linked in order 5' to 3';
        (i) A *Bombyx mori* nuclear polyhedrosis virus DNA (BmNPV DNA) polyhedrin promoter;
        (ii) BmNPV DNA encoding all or part of a polyhedral protein-encoding structural gene, with or without a linker base sequence coding for a linking peptide or amino acid;
        (iii) DNA encoding a structural gene for a desired protein positioned in a proper reading frame for all or part of said polyhedral protein-encoding structural gene; and
        (iv) a transcription terminator of said BmNPV DNA;
    (b) introducing said recombinant nuclear polyhedrosis virus into cells of a *Bombyx mori* cell line;
    (c) propagating said recombinant nuclear polyhedrosis virus; and
    (d) harvesting said desired protein and all or part of said polyhedral protein with or without said linking amino acid or peptide.

2. The method of claim 1, wherein the BmNPV DNA encoding all or part of a polyhedral protein-encoding structural gene consists of a fragment extending from base pair 4 to at least base pair 211 but not more than base pair 726.

3. The method of claim 2, wherein the fragment is selected from the group consisting of base pair 4 to base pair 211, base pair 4 to base pair 337, base pair 4 to base pair 661, and base pair 4 to base pair 726.

4. The method of claim 1, wherein the elements (i) to (iv) are derived from plasmid pIFNF086 which comprises a fragment of the polyhedral protein-encoding structural gene which comprises base pair 4 to base pair 726 and fused thereto a gene encoding α-interferon.

5. A method for producing a desired protein which comprises:
    (a) constructing a recombinant *Bombyx mori* nuclear polyhedrosis virus comprising the following elements, operatively linked in order 5' to 3';
        (i) a *Bombyx mori* nuclear polyhedrosis virus DNA (BmNPV DNA) polyhedrin promoter;
        (ii) BmNPV DNA encoding all or part of a polyhedral protein-encoding structural gene, with or without a linker base sequence coding for a linking peptide or amino acid;
        (iii) DNA encoding a structural gene for a desired protein positioned in a proper reading frame for all or part of said polyhedral protein-encoding structural gene; and
        (iv) A transcription terminator of said BmNPV DNA;
    (b) introducing said recombinant virus into cells of a *Bombyx mori* cell line;
    (c) propagating said recombinant nuclear polyhedrosis virus;
    (d) harvesting said desired protein and all or part of said polyhedral protein with or without said linking amino acid or peptide; and
    (e) cleaving said desired protein from all or part of said polyhedral protein with or without said linking amino acid or peptide.

6. The method of claim 5, wherein the BmNPV DNA encoding all or part of a polyhedral protein-encoding structural gene consists of a fragment extending from base pair 4 to at least base pair 211 but not more than base pair 726.

7. The method of claim 6, wherein the fragment is selected from the group consisting of base pair 4 to base pair 211, base pair 4 to base pair 337, base pair 4 to base pair 661, and base pair 4 to base pair 726.

8. The method of claim 5, wherein the elements (i) to (iv) are derived from plasmid pIFNF086 which comprises a fragment of the polyhedral protein-encoding structural gene which comprises base pair 4 to base pair 726 and fused thereto a gene encoding α-interferon.

9. A recombinant *Bombyx mori* nuclear polyhedrosis virus comprising the following elements, operatively linked, in order 5' to 3';
(a) a *Bombyx mori* nuclear polyhedrosis virus DNA (BmNPV DNA) polyhedrin promoter;
(b) BmNPV DNA encoding all or part of a polyhedral protein-encoding structural gene, with or without a linker base sequence coding for a linking peptide or amino acid;
(c) DNA encoding a structural gene for a desired protein positioned in a proper reading frame for all or part of said polyhedral protein-encoding structural gene; and
(d) a transcription terminator of said BmNPV DNA.

10. The recombinant *Bombyx mori* nuclear polyhedrosis virus of claim 9, wherein BmNPV DNA encoding all or part of a polyhedral protein-encoding structural gene consists of a fragment extending from base pair 4 to at least base pair 211 but not more than base pair 726.

11. The recombinant *Bombyx mori* nuclear polyhedrosis virus of claim 10, wherein the fragment is selected from the group consisting of base pair 4 to base pair 211, base pair 4 to base pair 337, base pair 4 to base pair 661, and base pair 4 to base pair 726.

12. The recombinant *Bombyx mori* nuclear polyhedrosis virus of claim 9, wherein the elements (a) to (d) are derived from plasmid pIFNF086 which comprises a fragment of the polyhedral protein-encoding structural gene which comprises base pair 4 to base pair 726 and fused thereto a gene encoding α-interferon.

13. A plasmid comprising the following elements, operatively linked in order 5' to 3':
(a) a *Bombyx mori* nuclear polyhedrosis virus DNA (BmNPV DNA) polyhedrin promoter;
(b) BmNPV DNA encoding all or part of a polyhedral protein-encoding structural gene, with or without a linker base sequence coding for a linking peptide or amino acid;
(c) DNA encoding a structural gene for a desired protein positioned in a proper reading frame for all or part of said polyhedral-encoding structural gene, and
(d) a transcription terminator of said BmNPV DNA.

14. The plasmid of claim 13, wherein the BmNPV DNA encoding all or part of a polyhedral protein-encoding structural gene consists of a fragment extending from base pair 4 to at least base pair 211 but not more than base pair 726.

15. The plasmid of claim 14, wherein the fragment is selected from the group consisting of base pair 4 to base pair 211, base pair 4 to base pair 337, base pair 4 to base pair 661, and base pair 4 to base pair 726.

16. The plasmid of claim 13 which is plasmid pIFNF086 which comprises a fragment of the polyhedral protein-encoding structural gene which comprises base pair 4 to base pair 726 and fused thereto a gene encoding α-interferon.

17. The plasmid of claim 18 which is plasmid pIFNF086 which comprises a fragment of the polyhedral protein-encoding structural gene which comprises base pair 4 to base pair 726 and fused thereto a gene encoding α-interferon.

18. The plasmid of claim 13, further comprising a linker base sequence coding for a linking peptide or amino acid interposed in a proper reading frame between all or part of said polyhedral protein-encoding structural gene and said structural gene for said desired protein.

19. The plasmid of claim 18, wherein the BmNPV DNA encoding all or part of a polyhedral protein-encoding structural gene consists of a fragment extending from base pair 4 to at least base pair 211 but not more than base pair 726.

20. The plasmid of claim 19, wherein the fragment is selected from the group consisting of base pair 4 to base pair 211, base pair 4 to base pair 337, base pair 4 to base pair 661, and base pair 4 to base pair 726.

21. A method of producing recombinant *Bombyx mori* nuclear polyhedrosis virus DNA which comprises:
cotransfecting a cultured *Bombyx mori* cell line or a strain of the *Bombyx mori* with a *Bombyx mori* nuclear polyhedrosis virus DNA (BmNPV DNA) and a plasmid comprising in order 5' to 3';
(a) a *Bombyx mori* nuclear polyhedrosis virus DNA (BmNPV DNA) polyhedrin promoter;
(b) BmNPV DNA encoding all or part of a polyhedral protein-encoding structural gene, with or without a linker base sequence coding for a linking peptide or amino acid;
(c) DNA encoding a structural gene for a desired protein positioned in a proper reading frame for all or part of said polyhedral-encoding structural gene; and
(d) a transcription terminator of said BmNPV DNA.

22. The method of claim 21, wherein the BmNPV DNA encoding all or part of a polyhedral protein-encoding structural gene consists of a fragment extending from base pair 4 to at least base pair 211 but not more than base pair 726.

23. The method of claim 22, wherein the fragment is selected from the group consisting of base pair 4 to base pair 211, base pair 4 to base pair 337, base pair 4 to base pair 661, and base pair 4 to base pair 726.

24. The method of claim 21, wherein said plasmid is plasmid pIFNF086 which comprises a fragment of the polyhedral protein-encoding structural gene which comprises base pair 4 to base pair 726 and fused thereto a gene encoding α-interferon.

25. The method of claim 21, wherein said plasmid further comprises a linker base sequence coding for a linking peptide or amino acid interposed in a proper reading frame between all or part of said polyhedral protein-encoding structural gene and said structural gene for said desired protein.

26. The method of claim 25, wherein the BmNPV DNA encoding all or part of a polyhedral protein-encoding structural gene consists of a fragment extending from base pair 4 to at least base pair 211 but not more than base pair 726.

27. The method of claim 26, wherein the fragment is selected from the group consisting of base pair 4 to base pair 211, base pair 4 to base pair 337, base pair 4 to base pair 661, and base pair 4 to base pair 726.

28. The method of claim 21, wherein said plasmid is plasmid pIFNF086 which comprises a fragment of the polyhedral protein-encoding structural gene which comprises base pair 4 to base pair 726 and fused thereto a gene encoding α-interferon.

* * * * *